US010222517B2

United States Patent
Gilad et al.

(10) Patent No.: US 10,222,517 B2
(45) Date of Patent: Mar. 5, 2019

(54) APERTURE STOP

(71) Applicant: Camtek Ltd., Migdal Haemeq (IL)

(72) Inventors: Tomer Gilad, Kiryat Tivon (IL); Shimon Koren, Haifa (IL)

(73) Assignee: CAMTEK LTD., Midgal Haemek (IL)

( * ) Notice: Subject to any disclaimer, the term of this patent is extended or adjusted under 35 U.S.C. 154(b) by 0 days.

(21) Appl. No.: 15/469,578

(22) Filed: Mar. 27, 2017

(65) Prior Publication Data

US 2017/0261654 A1    Sep. 14, 2017

Related U.S. Application Data

(63) Continuation-in-part of application No. 15/158,632, filed on May 19, 2016.

(60) Provisional application No. 62/175,315, filed on Jun. 14, 2015.

(51) Int. Cl.
| | |
|---|---|
| G02B 5/00 | (2006.01) |
| H04N 5/225 | (2006.01) |
| G02B 13/00 | (2006.01) |
| G01N 21/95 | (2006.01) |

(52) U.S. Cl.
CPC ......... *G02B 5/005* (2013.01); *G01N 21/9501* (2013.01); *G02B 13/0055* (2013.01); *H04N 5/2254* (2013.01); *H04N 5/2256* (2013.01)

(58) Field of Classification Search
CPC .......... G01N 21/00; G06T 2207/30148; H04N 5/2254; H06T 7/0004; G02B 13/0055
USPC ........................................................ 348/126
See application file for complete search history.

(56) References Cited

U.S. PATENT DOCUMENTS

| | | | | |
|---|---|---|---|---|
| 5,022,743 | A * | 6/1991 | Kino .................. | G02B 21/0044 359/235 |
| 7,295,303 | B1 * | 11/2007 | Vaez-Iravani .... | G01N 21/95623 356/237.1 |
| 9,140,544 | B2 * | 9/2015 | Barak ..................... | G01B 11/22 |
| 2003/0058454 | A1 * | 3/2003 | Scheiner .............. | G01B 11/254 356/601 |
| 2008/0144034 | A1 * | 6/2008 | Hill .................... | G01N 21/9501 356/445 |

* cited by examiner

*Primary Examiner* — William C Vaughn, Jr.
*Assistant Examiner* — Jae N Noh
(74) *Attorney, Agent, or Firm* — Reches Patents

(57) ABSTRACT

An aperture stop that includes a non-circular region that comprises at least one opaque region and at least one opening region; wherein each point in the at least one opening region is (a) mapped to an angle of illumination and (b) is associated with a corresponding point in the at least one opaque region that. mapped to an angle of specular reflectance from the angle of illumination mapped to the opening point.

39 Claims, 17 Drawing Sheets

450

APERTURE STOP

This application is a continuation in part of U.S. patent application Ser. No. 15/158,632 filing date May 19 2016 which claims the priority of U.S. provisional patent Ser. No. 62/175,315 filing date Jun. 14 2015 which is incorporated herein by reference.

BACKGROUND OF THE INVENTION 2D defect detection has two primary modes of sample illumination: bright field, which is insensitive to the topography of the wafer, and dark field, which is designed to collect scattered light and is therefore sensitive to the wafer topography and is especially useful for the identification of scratches.

All known dark field techniques illuminate the wafer at a large oblique angle. While suitable for a large range of applications, these techniques fail to enhance a class of defects which is characterized by local low angle inclination of the wafer. This class contains for example cracks and stresses in the wafer which modify the surface.

SUMMARY

According to an embodiment of the invention there may be provided an aperture stop that may include a circular region that may include multiple points, wherein the multiple points may include multiple opaque region points that may be spread across all polar angles and multiple opening points that may be spread across all polar angles; and wherein each opening point is (a) mapped to an angle of illumination and (b) is associated with a corresponding opaque region point that is mapped to an angle of specular reflectance from the angle of illumination mapped to the opening point.

Each opaque region point of a majority of the opaque region points may belong to an opaque region that is mapped to a small angular deviation from the angle of specular reflectance within an imaginary plane that includes a path of propagation of the specular reflectance.

The multiple opening points may be positioned within a majority of distances from a center of the circular region.

According to an embodiment of the invention there may be provided an aperture stop that may include a circular region that may include an opaque spiral area that is surrounded by one or more opening areas; and wherein each opening point is mapped to an angle of illumination and is associated with a corresponding opaque region point of the opaque spiral region that is mapped to an angle of specular reflectance from the angle of illumination mapped to the opening point.

According to an embodiment of the invention there may be provided an aperture stop that may include a circular region that may include at least one opaque area and at least one opening; and wherein for multiple distances from a center of the circular region and for each polar angle there is a pair of points that may include an oblique region point and an opening point that may be positioned at the distance from the center of the circular region and may belong to a diameter of the circular region that is oriented by the polar angle.

Each opening point may correspond to an angle of illumination and wherein each oblique region point may correspond to an angle of specular reflection.

A distance between each oblique region point and a closest opening point may correspond to a small angular deviation from the angle of specular reflection.

The small angular deviation does not exceed five degrees.

The at least one opaque area may include multiple opaque areas that have a radial symmetry; and wherein a majority of the opaque areas may be shaped as segments of a ring.

The at least one opaque area may include multiple opaque areas that have a radial symmetry; and wherein a majority of the multiple opaque areas span along an angular range that does not exceed ninety degrees.

The at least one opaque area is a spiral shaped opaque area.

The at least one opaque area is an approximation of a spiral.

According to an embodiment of the invention there may be provided an inspection system that may include a light source, an objective lens and an aperture stop; wherein the light source is configured to illuminate the aperture stop; wherein the aperture stop is positioned at a stop of the objective lens; wherein at least one of the following is true: (i) the aperture stop may include a circular region that may include multiple points, wherein the multiple points may include multiple opaque region points that may be spread across all polar angles and multiple opening points that may be spread across all polar angles; and wherein each opening point is (a) mapped to an angle of illumination and (b) is associated with a corresponding opaque region point that is mapped to an angle of specular reflectance from the angle of illumination mapped to the opening point; (ii) the aperture stop may include a circular region that may include an opaque spiral area that is surrounded by one or more opening areas; and wherein each opening point is mapped to an angle of illumination and is associated with a corresponding opaque region point of the opaque spiral region that is mapped to an angle of specular reflectance from the angle of illumination mapped to the opening point; and (iii) the aperture stop may include a circular region that may include at least one opaque area and at least one opening; and wherein for multiple distances from a center of the circular region and for each polar angle there is a pair of points that may include an oblique region point and an opening point that may be positioned at the distance from the center of the circular region and may belong to a diameter of the circular region that is oriented by the polar angle.

According to an embodiment of the invention there may be provided a method that may include illuminating an apertures stop that is located at a stop of an objective lens; illuminating an object by light that passes through the aperture stop and an objective lens; collecting, by the objective lens, reflected light that passes through the aperture stop, the reflected light differs from specular reflection light; and directing the reflected light that passes through the aperture stop towards a detector; wherein at least one of the following is true: (i) the aperture stop may include a circular region that may include multiple points, wherein the multiple points may include multiple opaque region points that may be spread across all polar angles and multiple opening points that may be spread across all polar angles; and wherein each opening point is (a) mapped to an angle of illumination and (b) is associated with a corresponding opaque region point that is mapped to an angle of specular reflectance from the angle of illumination mapped to the opening point; (ii) the aperture stop may include a circular region that may include an opaque spiral area that is surrounded by one or more opening areas; and wherein each opening point is mapped to an angle of illumination and is associated with a corresponding opaque region point of the opaque spiral region that is mapped to an angle of specular reflectance from the angle of illumination mapped to the opening point; and (iii) the aperture stop may include a circular region that may include at least one opaque area and at least one opening; and wherein for multiple distances from a center of the circular region and for each polar angle there is a pair of points that may include an oblique region point and an opening point that may be positioned at the distance from the center of the circular region and may belong to a diameter of the circular region that is oriented by the polar angle.

There may be provided an aperture stop may include a non-circular region that may include multiple points, the multiple points may include multiple opaque region points and multiple opening points each opening point may be (a) mapped to an angle of illumination and (b) may be associated with a corresponding opaque region point that may be mapped to an angle of specular reflectance from the angle of illumination mapped to the opening point. The non-circular region may be elliptical (but not circle), a polygon, or may have any other shape. The non-circular region may have non-linear border portions, a combination of linear and non-linear border portions, and the like.

Each opaque region point of a majority of the opaque region points may belong to an opaque region that may be mapped to a small angular deviation (for example, 2, 3, 4, 5 angles and the like) from the angle of specular reflectance within an imaginary plane that includes a path of propagation of the specular reflectance.

The multiple opening points may form at least one opening that may be a polygon.

The multiple opening points may form a triangle shaped opening and a trapezoid shaped opening.

The multiple opaque points may form a triangle shaped opaque region and a trapezoid shaped opaque region.

The non-circular region may have an axis of asymmetry the triangle shaped opening and the trapezoid shaped opaque region may be positioned at one side of the axis of asymmetry the triangle shaped opaque region and the trapezoid shaped opening may be positioned at another side of the axis of asymmetry.

There may be provided an aperture stop may include a circular region that may include multiple points, the multiple points may include multiple opaque region points and multiple opening points each opening point may be (a) mapped to an angle of illumination and (b) may be associated with a corresponding opaque region point that may be mapped to an angle of specular reflectance from the angle of illumination mapped to the opening point. The multiple opening points may form multiple openings. The multiple openings may include a certain opening that may have a border that may include at least one linear border portion and at least one non-linear border portion.

The certain opening may have a shape that differs from a combination of arcs.

The circular region may have an axis of symmetry the multiple openings may be symmetric in relation to the axis of symmetry.

The circular region may include an interior circular portion that may be surrounded by an exterior ring. A plurality of interior opening portions may be positioned within the interior circular portion. A plurality of exterior opening portions may be positioned within the exterior ring.

The aperture stop further may include at least one opening within at least one of the interior circular portion and the exterior ring.

The each one of the interior opening portions may be delimited by at least one secant line and by an edge of the interior circular portion.

The each one of the exterior opening portions may be delimited by at least one radial line, by an interior edge and by an exterior edge of the exterior ring.

The three exterior opening portions and two exterior openings may be located within the exterior ring and two interior opening portions may be located within the interior circular region.

There may be provided an aperture stop may include a region that may include at least one opaque area and at least one opening. For multiple distances from an axis of the region and for multiple positioned along the axis there may be a pair of points that may include an oblique region point and an opening point that may be positioned at the distance from the axis of the region.

The apertures top the axis of the region may be selected out of an axis of symmetry and an axis of asymmetry.

Each opening point may correspond to an angle of illumination and each oblique region point may correspond to an angle of specular reflection.

The distance between each oblique region point and a closest opening point may correspond to a small angular deviation from the angle of specular reflection.

The small angular deviation does not exceed five degrees.

There may be provided an aperture stop that may include a circular region that may include at least one opaque region and at least one opening region; wherein each point in the at least one opening region is (a) mapped to an angle of illumination and (b) is associated with a corresponding point in the at least one opaque region that. mapped to an angle of specular reflectance from the angle of illumination mapped to the opening point; wherein the at least one opening region comprise a certain opening region that has a border that may include at least one linear border portion and at least one non-linear border portion.

For each point in the at least one opening region the corresponding point in the at least one opaque region is symmetric in relation to a center of the non-circular region as the point in the at least one opening region. Symmetric may mean positioned at the same distance from the center of the non-circular region, at opposite side and along a virtual line that passes through the center of the non-circular region as well as the point in the at least one opening region and the corresponding point in the at least one opaque region.

There may be provided an aperture stop that may include a non-circular region that may include at least one opaque region and at least one opening region; wherein each point in the at least one opening region is (a) mapped to an angle of illumination and (b) is associated with a corresponding point in the at least one opaque region that. mapped to an angle of specular reflectance from the angle of illumination mapped to the opening point.

There may be provided an inspection system that may include a light source, an objective lens and an aperture stop. The light source may be configured to illuminate the aperture stop the aperture stop may be positioned at a stop of the objective lens. In addition, at least one of the following may be true:

a. The aperture stop may include a non-circular region that may include multiple points. the multiple points may include multiple opaque region points and multiple opening points. Each opening point may be (a) mapped to an angle of illumination and (b) may be associated with a corresponding opaque region point that may be mapped to an angle of specular reflectance from the angle of illumination mapped to the opening point.

b. The aperture stop may include a circular region that may include multiple points. The multiple points may include multiple opaque region points and multiple opening points. Each opening point may be (a) mapped to an angle of illumination and (b) may be associated with a corresponding opaque region point that may be mapped to an angle of specular reflectance from the angle of illumination mapped to the opening point. The multiple opening points may form multiple openings. The multiple openings may include a certain opening that may have a border that may include at least one linear border portion and at least one non-linear border portion.

c. The aperture stop may include a region that may include at least one opaque area and at least one opening. For multiple distances from an axis of the region and for multiple positioned along the axis there may be a pair of points that may include an oblique region point and an opening point that may be positioned at the distance from the axis of the region.

There may be provided a method that may include: (a) illuminating an apertures stop that may be located at a stop of an objective lens; (b) illuminating an object by light that passes through the aperture stop and an objective lens; (c) collecting, by the objective lens, reflected light that passes through the aperture stop, the reflected light differs from specular reflection light; and (d) directing the reflected light that passes through the aperture stop towards a detector. In addition, at least one of the following may be true:

a. The aperture stop may include a circular region that may include at least one opaque region and at least one opening region; wherein each point in the at least one opening region is (a) mapped to an angle of illumination and (b) is associated with a corresponding point in the at least one opaque region that. mapped to an angle of specular reflectance from the angle of illumination mapped to the opening point; wherein the at least one opening region comprise a certain opening region that has a border that may include at least one linear border portion and at least one non-linear border portion.

b. The aperture stop may include a non-circular region that may include at least one opaque region and at least one opening region; wherein each point in the at least one opening region is (a) mapped to an angle of illumination and (b) is associated with a corresponding point in the at least one opaque region that. mapped to an angle of specular reflectance from the angle of illumination mapped to the opening point.

c. The aperture stop may include a region that may include at least one opaque area and at least one opening; and wherein for multiple distances from an axis of the region and for multiple positioned along the axis there is a pair of points that may include an oblique region point and an opening point that are positioned at the distance from the axis of the region.

BRIEF DESCRIPTION OF THE INVENTION

The present invention will be understood and appreciated more fully from the following detailed description taken in conjunction with the drawings in which.

DETAILED DESCRIPTION OF THE INVENTION

Because the apparatus implementing the present invention is, for the most part, composed of optical components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

In the following specification, the invention will be described with reference to specific examples of embodiments of the invention. It will, however, be evident that various modifications and changes may be made therein without departing from the broader spirit and scope of the invention as set forth in the appended claims.

The term "specular reflection" refers (wikipedia.org) to a mirror-like reflection of light from a surface, in which the direction of incoming light (the incident ray), and the direction of outgoing light reflected (the reflected ray) make the same angle with respect to the surface normal, thus the angle of incidence equals the angle of reflection ($\theta_i = \theta_r$ in the figure), and that the incident, normal, and reflected directions are coplanar.

There is provided an aperture stop that provides a mean to modify a microscope objective so that when used in bright field, it effectively creates a low angle dark field illumination, enabling the detection of the class of defects mentioned above.

The aperture stop may include shifted arcs, allows low angle specular reflections (in which there is a small angular difference of few angles between the angle of incidence and the angle of reflection) to pass back to the camera while blocking the specular reflection (in which the angle of incidence equals the angle of reflection) from the flat surfaces. Therefore defects which are manifested as local wafer inclination are seen as bright, high contrast shapes relative to their surroundings.

Figure 1:
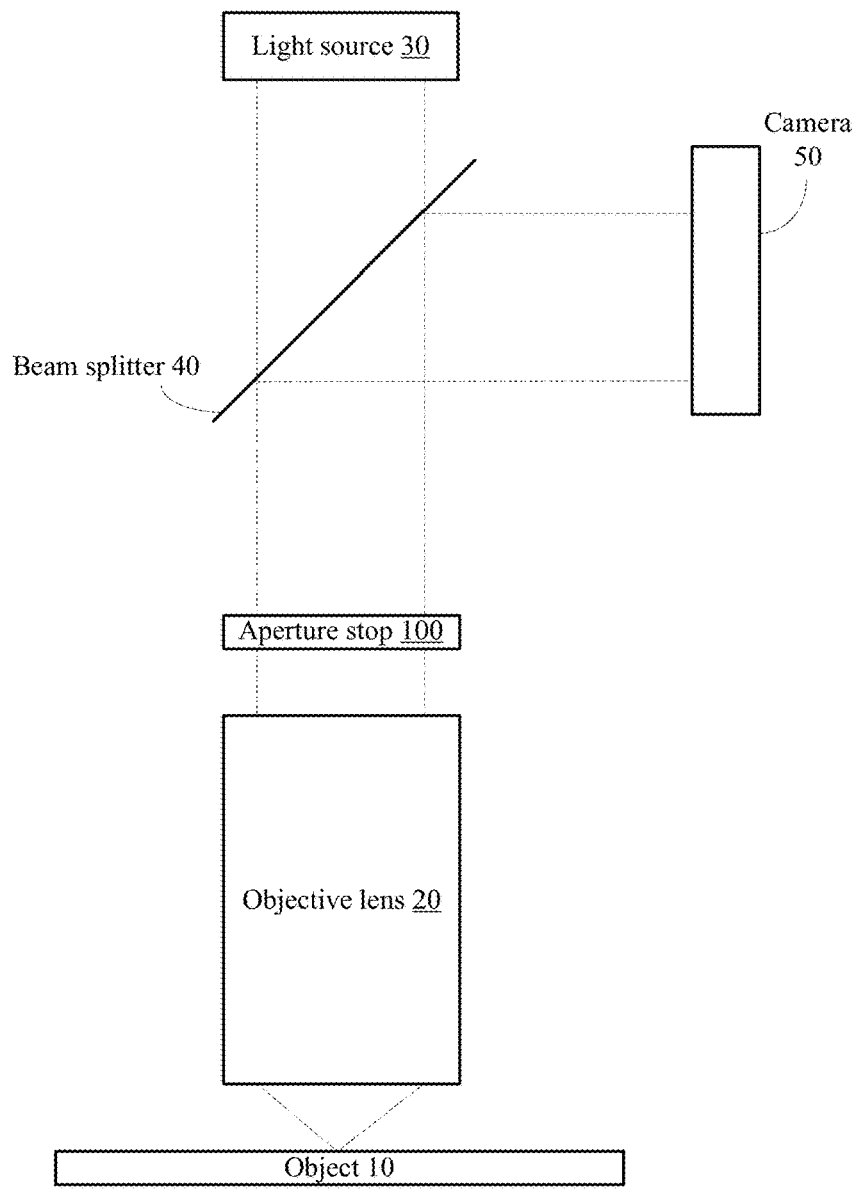
FIG. 1 illustrates an object, a light source, a beam splitter, an aperture stop and a camera according to an embodiment of the invention.
Figure 2:
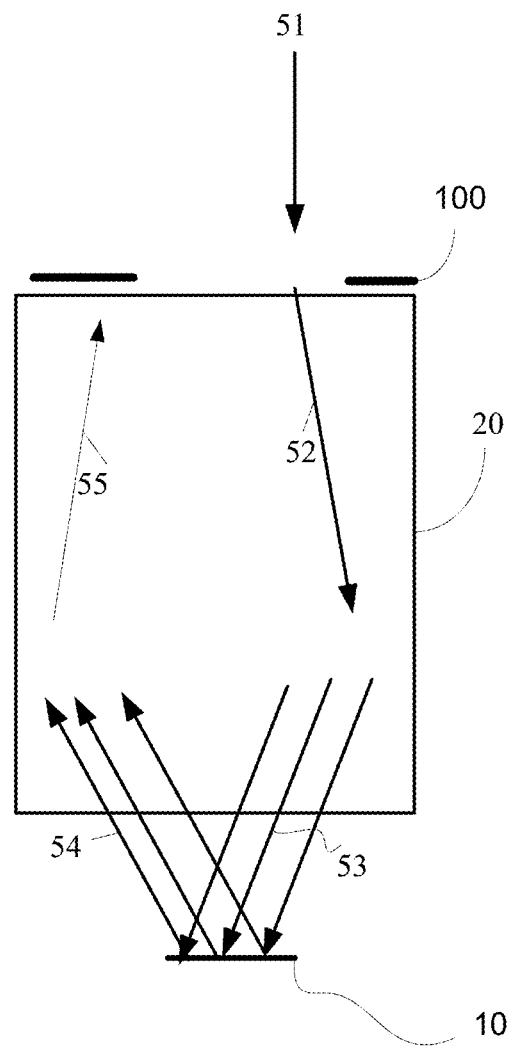
FIG. 2 illustrates an object, an objective lens, an aperture stop and a blocked light beam according to an embodiment of the invention.

FIG. 1 illustrates an object 10, a light source 30, a beam splitter 40, an aperture stop 100, an objective lens 20 and a camera 50 according to an embodiment of the invention. Light from light source 30 passes through beam splitter 40 and is partially blocked by one or more opaque blocks of aperture stop 100. Light that passes through one or more opening s of the aperture stop pass through objective lens 20 to be directed onto object 10.

It should be noted that each incident light ray that passes through each opening point of an opening of the aperture stop 100 diverges and illuminates the entire field of view (object). Each point in the field of view receives contributions from all points in the one or more opening (this is due to the special position where the stop is located and the design of typical microscope illumination, i.e. Kohler illumination).

Light reflected from the object 10 is collected by objective lens 20. Reflected light rays that are the specular reflectance of any incident light ray are blocked by the aperture stops. Reflected light rays that are not the specular reflectance of any of the incident light rays pass through the apertures top and are directed by beam splitter 40 towards camera.

The aperture stop is located at the stop of the objective lens 20. The objective lens 20 is mounted normally on the microscope.

Because the aperture stop is positioned at the objective stop each point of the aperture stop is mapped to an angle of incidence (for incoming light rays) for illuminating the entire field of view or to an angle of reflectance (for reflected light rays). Especially—the center of the aperture stop may correspond to normal angle of incidence and normal angle of reflectance. The distance between any point of the aperture stop and the center of the aperture stop defines the value of the angle of incidence (angle of reflectance).

The specular reflected beam from the object is mapped to a field point in the aperture stop which is symmetrical (in relation to the center of the aperture stop) to the initial field point (incident beam).

Figure 3:
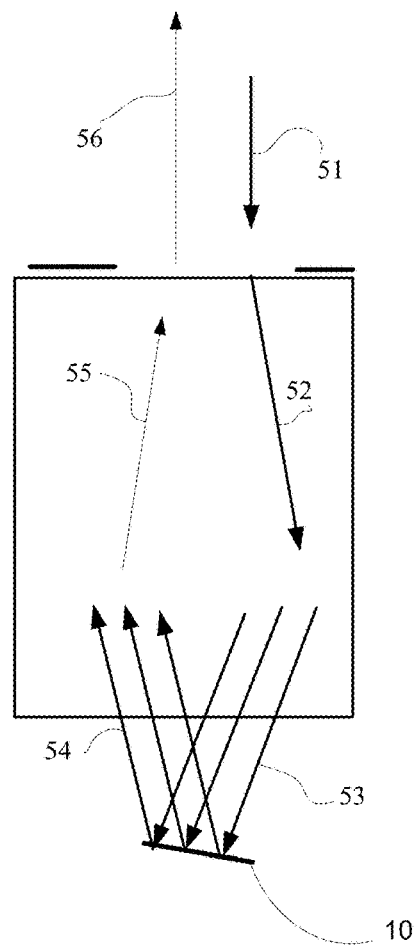
FIG. 3 illustrates an object, an objective lens an aperture stop and an unblocked light beam according to an embodiment of the invention.

The aperture stop is placed at the stop of the objective. Its asymmetrical structure blocks the returning path of specular reflectance rays from the object under normal conditions. FIG. 3 illustrates incoming ray 51 that is deflected rightwards (arrow 52) and then deflected leftwards (rays 53) within the objective lens and impinges on (a horizontal) object 10. Reflected rays (arrows 54) which are the specular reflection of rays 53 are deflected leftwards and the deflected rightwards (ray 55) to be blocked by an opaque area of aperture stop 100.

However, light from locally tilted regions in the object (the wafer) are reflected at a diverted angle relative to the optical axis. The light is further mapped to a point in the stop that is not symmetrical to the incoming ray. The asymmetry of the aperture stop intentionally captures these diverted rays. This is illustrated in FIG. 3 where ray of light 55 is not blocked by the aperture stop 100 and ray of light 56 exits from the objective lens.

Hence the effect of the aperture stop is to enhance low angle surface tilts while diminishing the reflection from the flat regions, leading to high contrast of low angle defects. The detailed design of the aperture stop allows optimizing it to applications based on the typical surface tilts which are exhibited.

The aperture stop may be a thin solid disk or at least may include a circular region that may be surrounded by a frame. For simplicity of explanation it will be assumed that the aperture stop has a circular shape.

The aperture stop includes one or more opaque areas to light, having certain openings which allow light passage.

Figure 4:
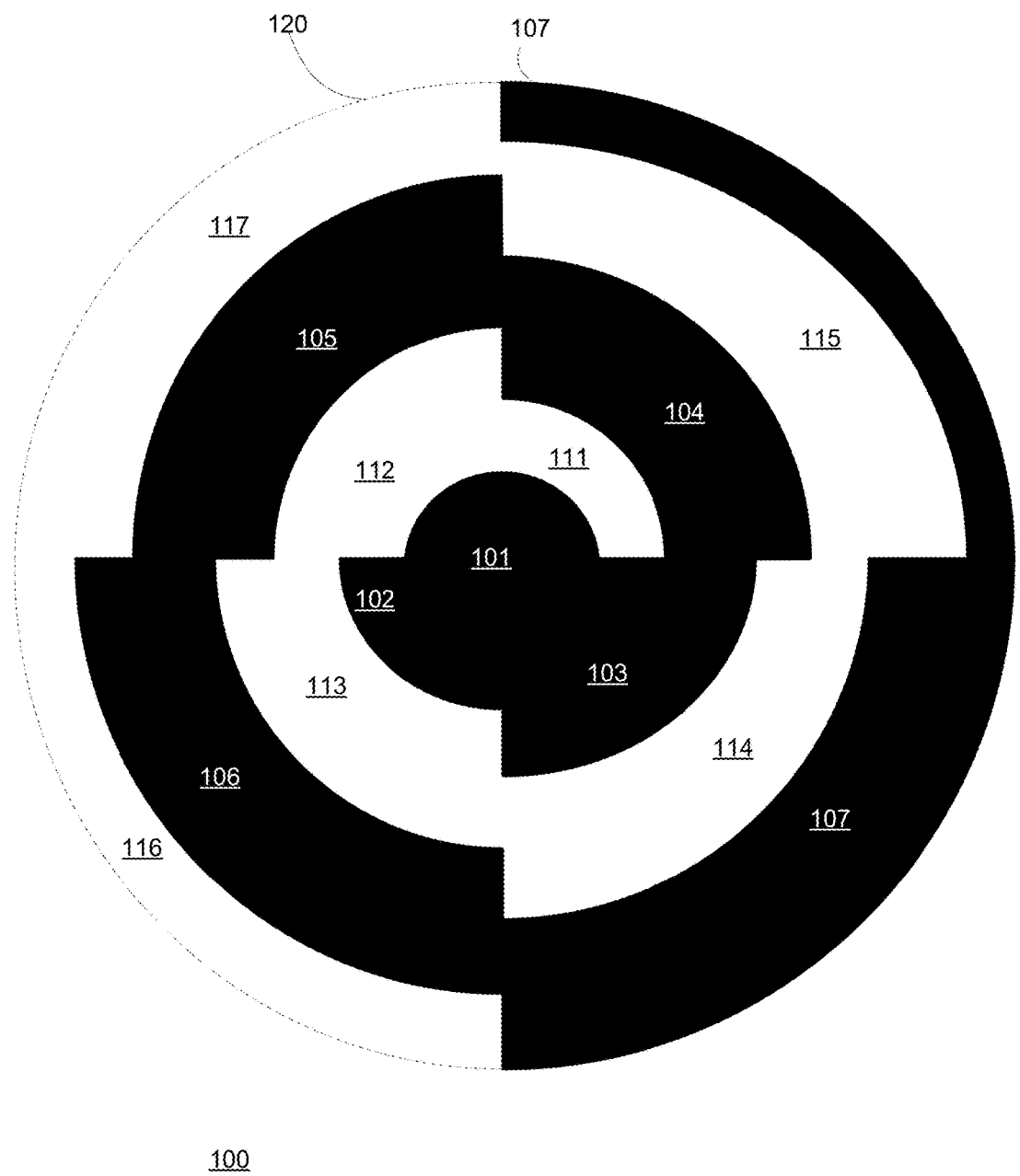
FIG. 4 illustrates an aperture stop according to an embodiment of the invention.

FIG. 4 illustrates an aperture stop 100 according to an embodiment of the invention. Within a circular region 120 there are opaque areas 101-107 and opening s 111-117.

Figure 5:
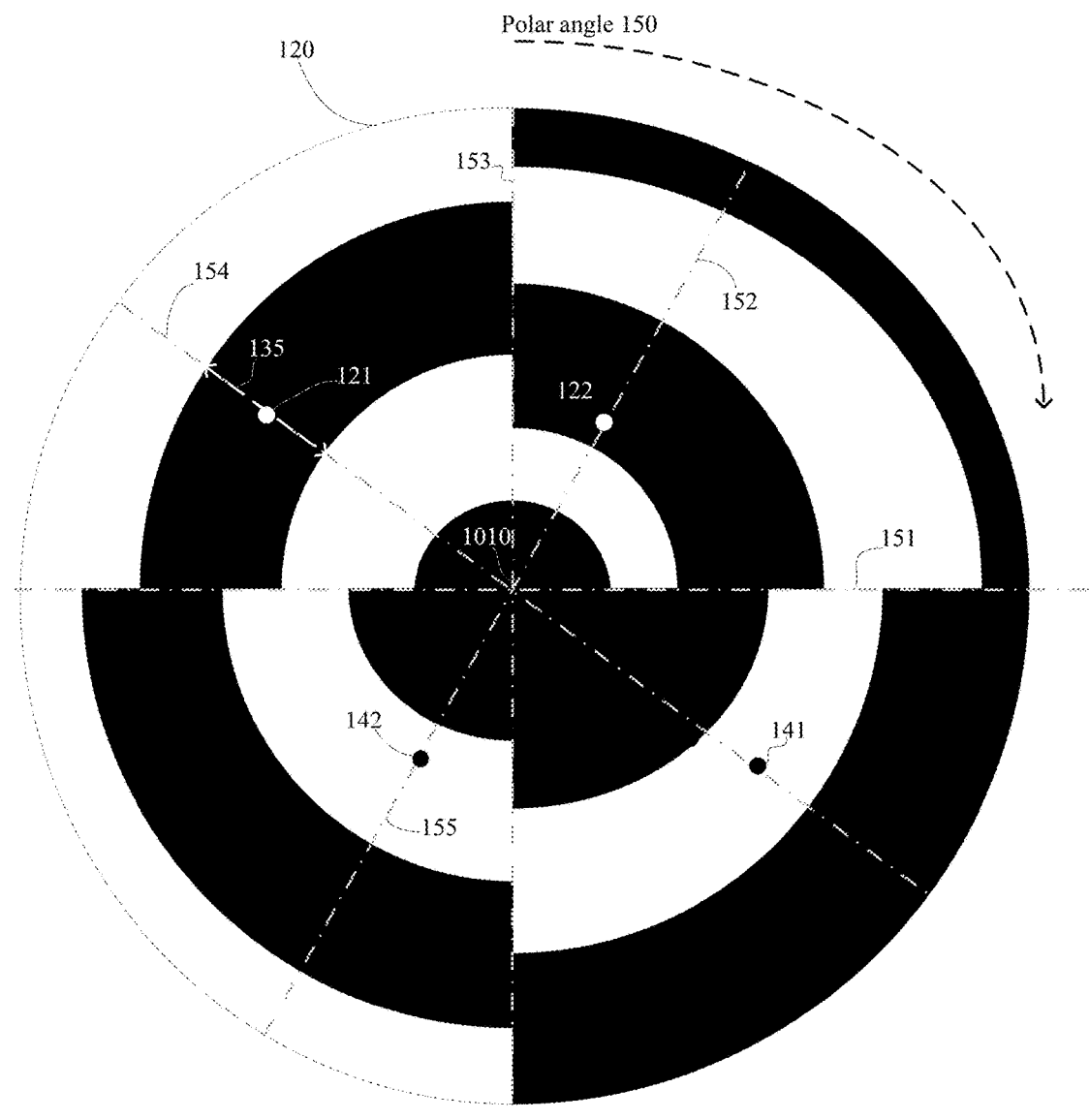
FIG. 5 illustrates an aperture stop according to an embodiment of the invention.

The bright regions are the material and the black voids are the openings. The structure of the openings is such that, when viewed at a radial cross section, there are alternating areas of material and openings. In addition, at any given angle, points of equal distance (i.e. the same radius) from the center of the aperture stop are made of opposite materials (one belongs to an opening and the other belongs to an opaque area). It should be noted that, there are some advantages to retain a low specular reflection for improving the process of building the wafer map. This allows a full wafer scan and requires die to die alignment, etc., which can improve with a low specular reflection FIG. 5 illustrates that for each point of incidence (141 and 142) within an opening there is a corresponding point of specular reflectance (121 and 122) that is blocked by an opaque area. The corresponding point and the point of incidence "belong" to the same virtual diameter (152 and 154). This is true for all polar angles (for any diameter of any orientation—such as but not limited to diameters 151, 152, 153 and 154)). Outside opaque area 101 there is a symmetry between opaque points and opening points.

FIG. 5 also illustrates that each opaque area is narrow from a radial point of view-if spans along a limited angular range. This enables reflected rays from surface with a small tilt (in relation the horizon) to pass through the aperture stop 100. Typical values had a peak response at 0.5 degree, and a meaningful response between 0.3 degrees to 1 degree, with a very low specular response at 0 degrees.

The outer diameter of the aperture stop should match the diameter of the objective lens. The center of the aperture can be either open or full.

Figure 6:
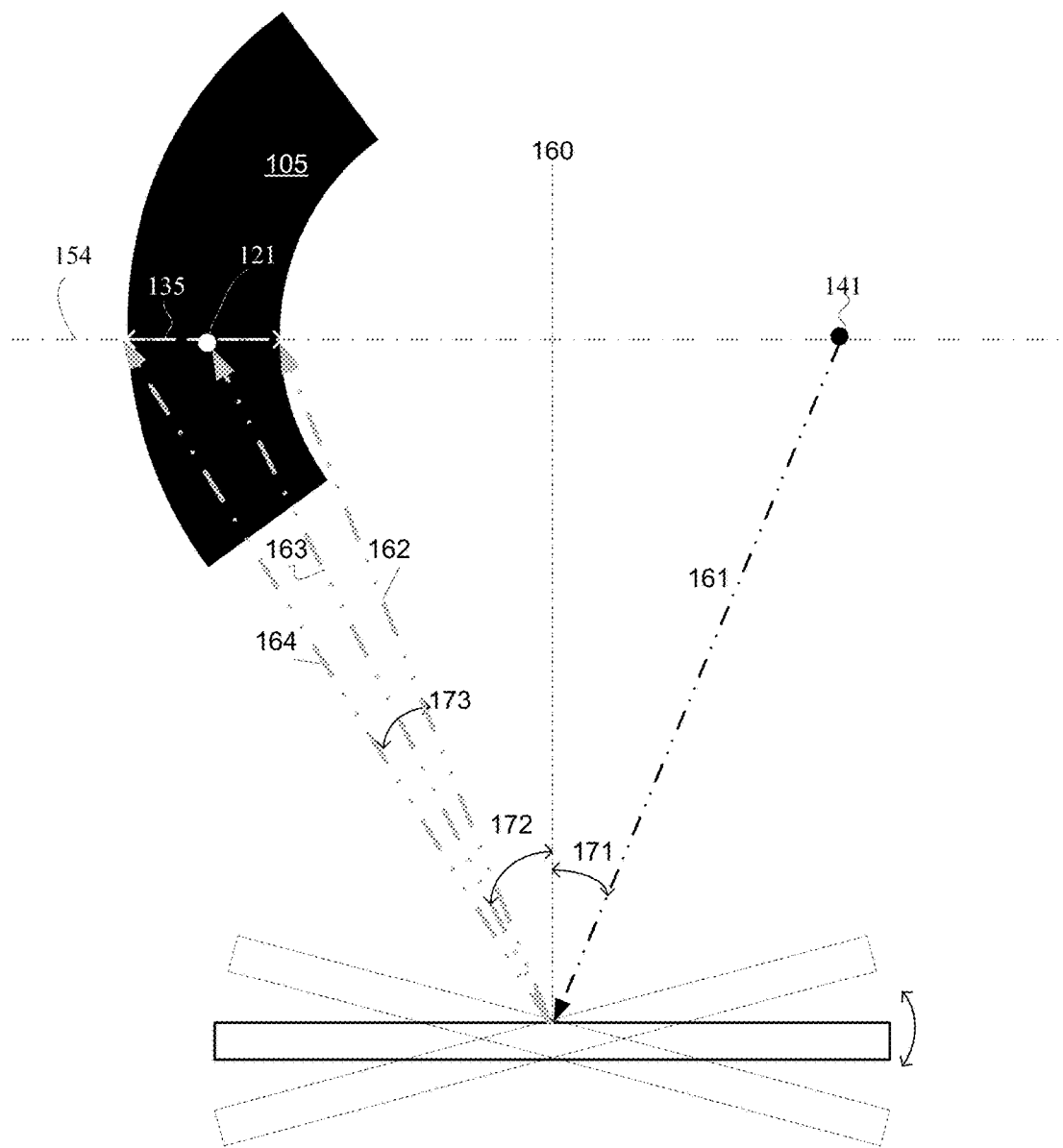
FIG. 6 illustrates an aperture stop and some blocked beams according to an embodiment of the invention.

FIG. 6 illustrates a mapping between opening point 141, a corresponding opaque 121, and angles of reflection that slightly deviate from the specular reflection angle, according to an embodiment of the invention.

Ray 161 impinges through point 141 and has an angle of incidence 171. When the illuminated object (illuminated point of the object) is horizontal the reflected ray 163 is reflected at an angle of reflection 172 that equals angle of incidence 171. Reflected ray 163 is blocked by opaque area 121. The width 135 of opaque area 121 is tailored in order to block reflected rays that are confided to a small angular deviation 173 from angle of reflection 172. Reflected rays 162 and 164 (reflected from tilted areas of the wafer-illustrated by tilted boxes) are not blocked by opaque area 121 and pass near the borders of opaque area 121.

Figure 7:
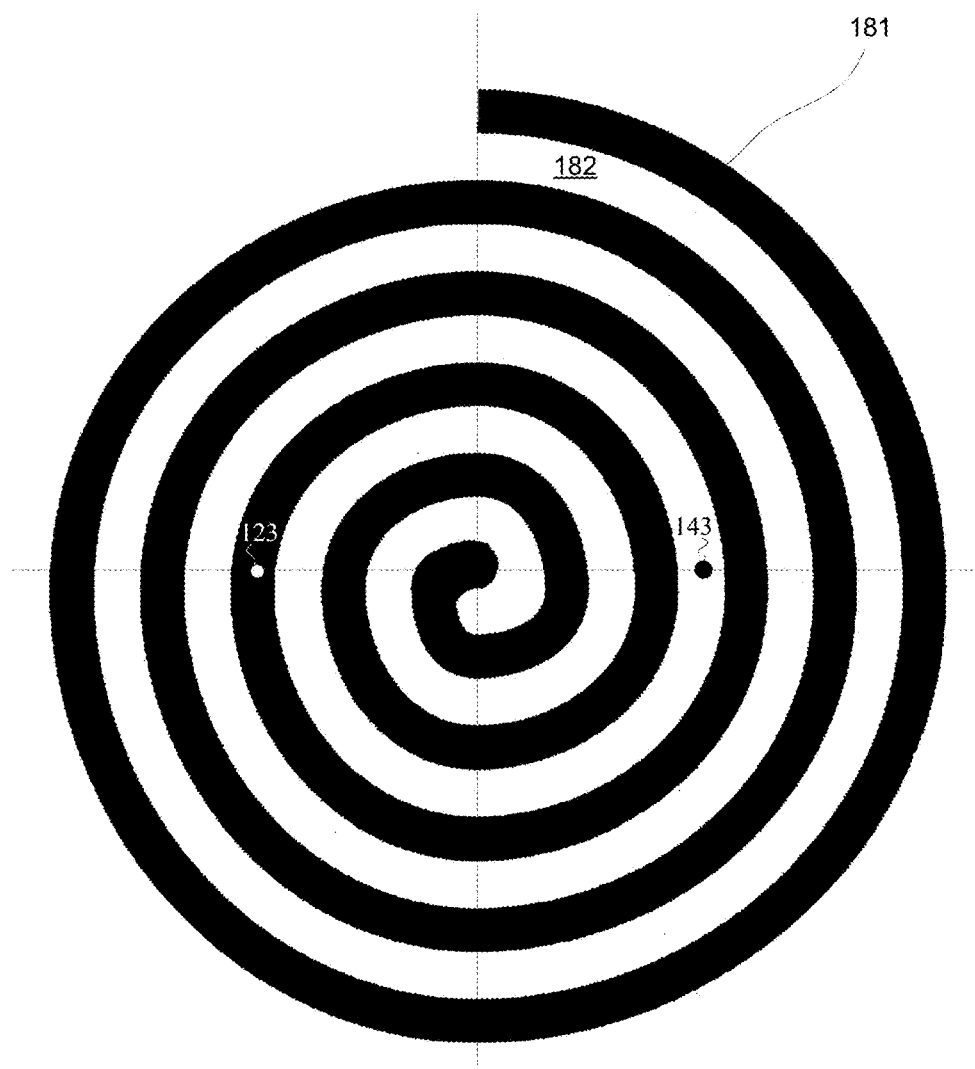
FIG. 7 illustrates an aperture stop according to an embodiment of the invention.

FIG. 7 illustrates an aperture stop 100 according to an embodiment of the invention.

Aperture stop 100 includes opaque spiral area 181 that is surrounded by one or more opening areas 182. Each opening point (such as 143) is mapped to an angle of illumination and is associated with a corresponding opaque region point (such as point 123) of the opaque spiral area that is mapped to an angle of specular reflectance from the angle of illumination mapped to the opening point. The width of the opaque spiral area 181 may be tailored such as not to block reflections that are not specular reflections and deviate from the specular reflection by few degrees.

Figure 8:
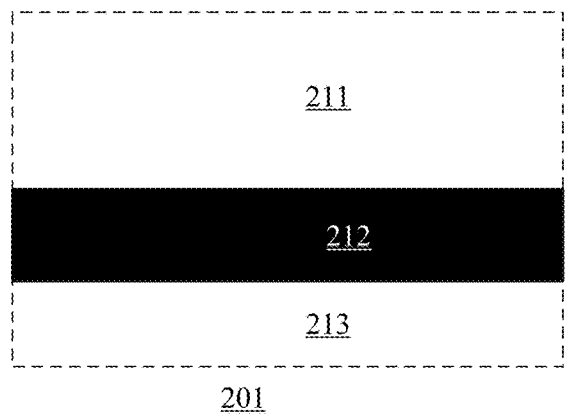
FIG. 8 illustrates flat, specular reflective regions of two different dies, a gap between the dies with or without a chipping defect and a crack defect that are proximate to the gap.
Figure 8:
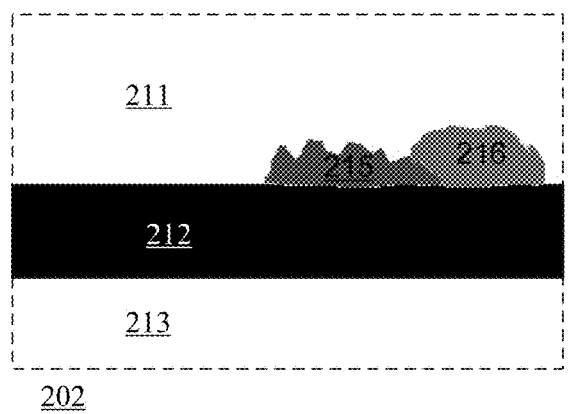

FIG. 8 illustrates, in box 201 two regions 211 and 213 of two different dies and a gap 212 between these regions. Regions 211 and 213 may belong to different dies.

FIG. 8 illustrates, in box 202 two regions 211 and 213 (that are flat, horizontal and specular reflective) of two different dies and a gap 212 between these regions. Regions 211 and 213 may belong to different dies. Box 202 also illustrates a chipping defect 215 and a crack defect 216 that are proximate to gap 212. An inner crack within the wafer may slightly lift (or tilt) a part of the wafer thereby resulting in a crack defect 216 that has a upper surface that is slightly tilted in relation to the horizon.

Figure 9:
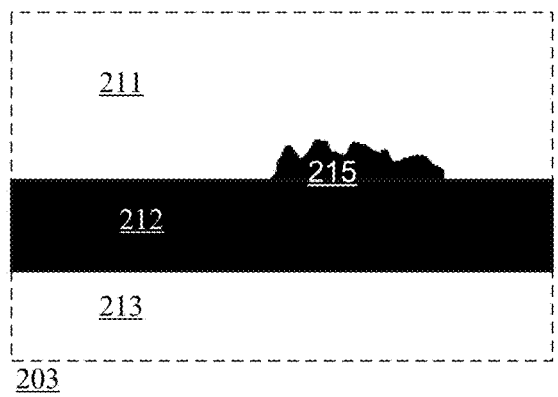
FIG. 9 illustrates images of the flat, specular reflective regions of two different dies, a gap between the dies with a chipping defect and a crack defect that are proximate to the gap.
Figure 9:
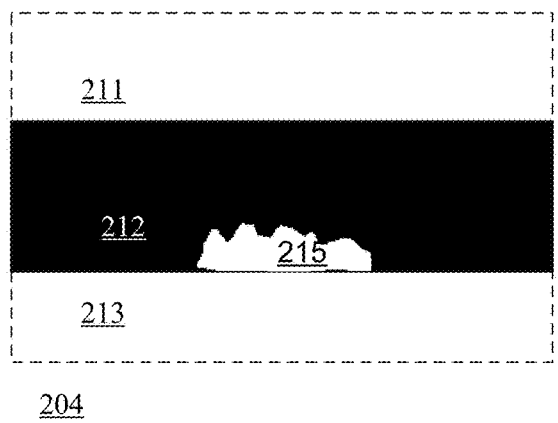
Figure 9:
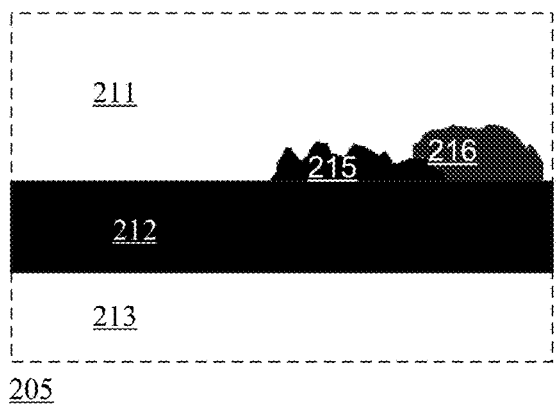

FIG. 9 illustrates images 203, 204 and 205 of the flat, specular reflective regions of two different dies, a gap between the dies with a chipping defect and a crack defect that are proximate to the gap.

Image 203 is acquired using bright field illumination. In image 203 the proper reflection of metal is bright. A dark region indicates missing material—this is a chipping defect 215. The crack is not observable.

Image 204 is acquired using dark field illumination. In image 204 the proper reflection of metal is dark. The missing material appears bright due to the reflections from the edges—the chipping defect 215 is detected as a bright region. The crack defect is not observable due to its low tilt angle.

Image 205 is acquired by using a circular aperture stop with a diameter which is appreciably smaller than the effective pupil diameter. The circular aperture stop is placed at the pupil of the objective lens. Such circular aperture stop enables to detect crack defects, but the crack defects 216 appear dark it is hard to distinguish them from the chipping defects 215.

Figure 10:
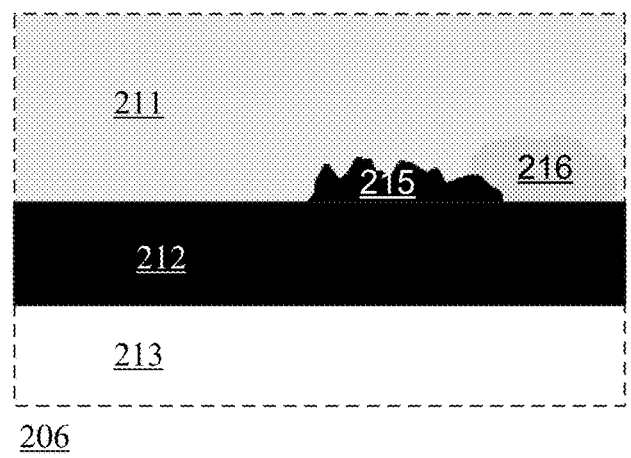
FIG. 10 illustrates an image of the flat, specular reflective regions of two different dies, a gap between the dies with a chipping defect and a crack defect that are proximate to the gap according to an embodiment of the invention.

FIG. 10 illustrates image 206 according to an embodiment of the invention.

In image 206 the proper metal reflection is low (due to the blocking of the specular reflectance), the chipping defect 215 is much darker that the clearly visible crack defect 216 that is brighter than the chipping defect 251, regions 211 and 213 and gap 212.

Figure 11:
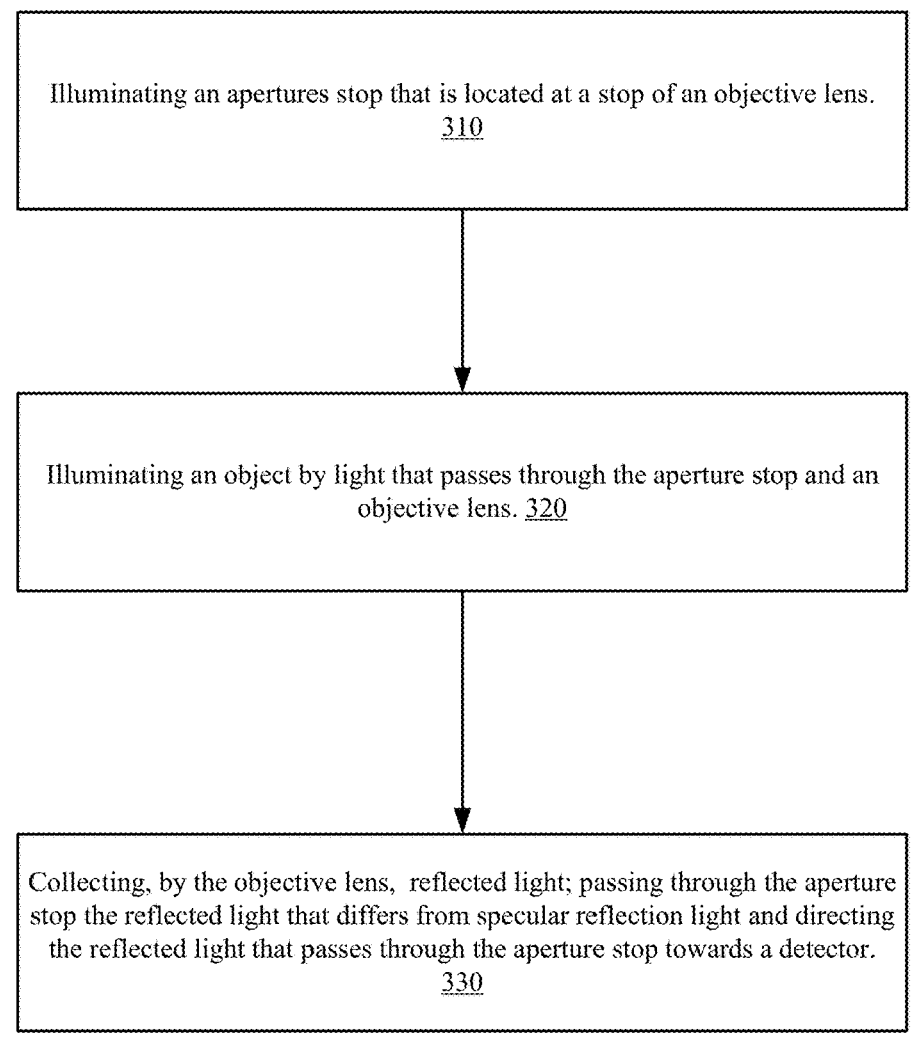
FIG. 11 illustrates a method according to an embodiment of the invention.

FIG. 11 illustrates method 300 according to an embodiment of the invention.

Method 300 may start by step 310 of illuminating an aperture stop that is located at a stop of an objective lens.

Step 310 may be followed by step 320 of illuminating an object by light that passes through the aperture stop and an objective lens.

Step 320 may be followed by step 330 of collecting, by the objective lens, reflected light; passing through the aperture stop the reflected light that differs from specular reflection light and directing the reflected light that passes through the aperture stop towards a detector.

The aperture stop referred to in steps 310 and 320 may be any of the apertures stops mentioned in the specification—including but not limited to FIGS. 4-5, 7, and 12-16.

Regarding the aperture stop—any statement made in the summery or any other part of the specification about the aperture stop can be applied to the aperture stop that is illuminated in step 310.

For example—at least one of the following is true:
(i) the aperture stop comprises a circular region that comprises at least one opaque region and at least one opening region; wherein each point in the at least one opening region is (a) mapped to an angle of illumination and (b) is associated with a corresponding point in the at least one opaque region that. mapped to an angle of specular reflectance from the angle of illumination mapped to the opening point; wherein the at least one opening region comprise a certain opening region that has a border that comprises at least one linear border portion and at least one non-linear border portion;
(ii) the aperture stop comprises a non-circular region that comprises at least one opaque region and at least one opening region; wherein each point in the at least one opening region is (a) mapped to an angle of illumination and (b) is associated with a corresponding point in the at least one opaque region that. mapped to an angle of specular reflectance from the angle of illumination mapped to the opening point;
(iii) the aperture stop comprises a region that comprises at least one opaque area and at least one opening; and wherein for multiple distances from an axis of the region and for multiple positioned along the axis there is a pair of points that comprises an oblique region point and an opening point that are positioned at the distance from the axis of the region.

Figure 12:
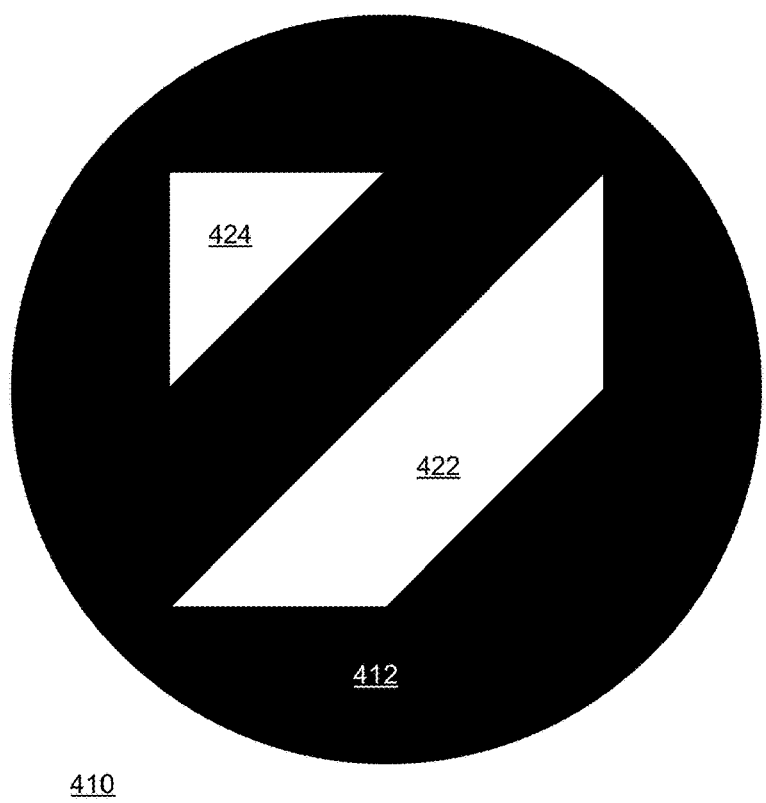
FIG. 12 illustrates an aperture stop according to an embodiment of the invention.
Figure 12:
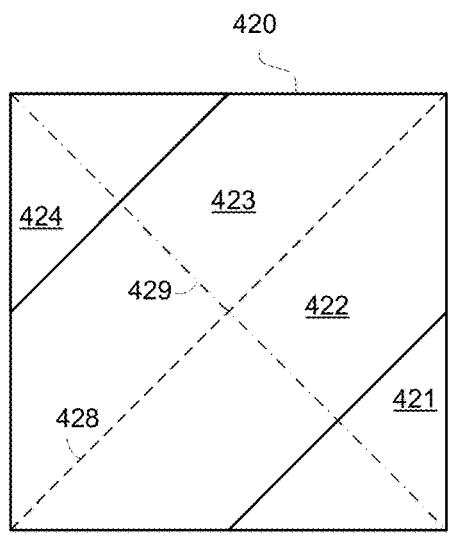

FIG. 12 illustrates an aperture stop 410 that include a non-circular region that is shaped as a square 420 that include a triangle shaped opening 424 and a trapezoid shaped opening 422 that are surrounded by opaque region 412.

Square 420 has a symmetry axis 428 (oriented in −45 degrees) and an asymmetry axis 428 that is oriented in 45 degrees.

Asymmetry axis 428 is referred to as an asymmetry axis because within square 420 each opening point that is located at one side of the asymmetry axis has a corresponding opaque point that is located at a mirror location—at the other side of the asymmetry axis.

Triangle shaped opening 424 is "mirrored" by a triangle shaped opaque region 421. Trapezoid shaped opening 422 is "mirrored" by a trapezoid shaped opaque region 423.

Figure 13:
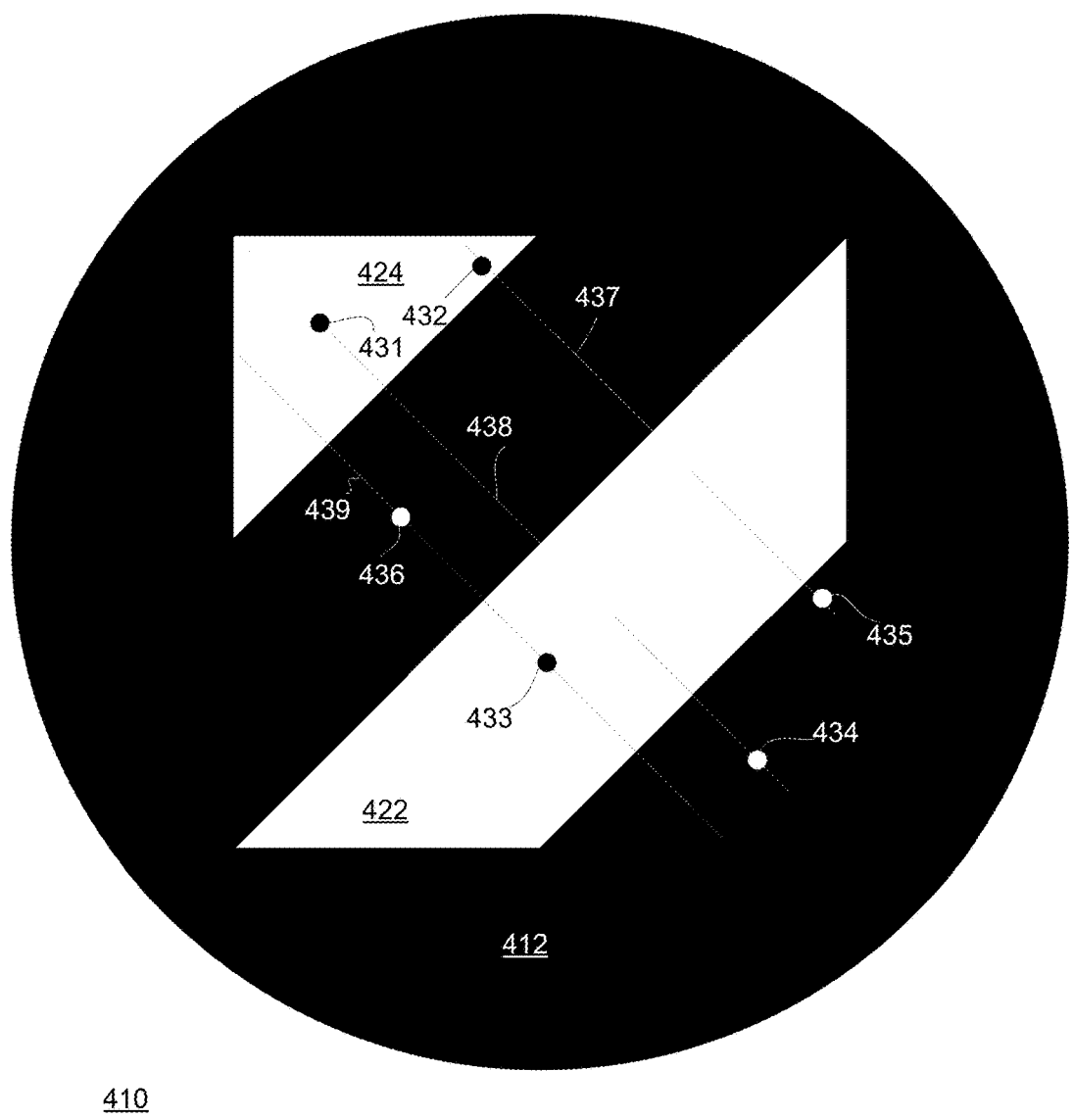
FIG. 13 illustrates an aperture stop according to an embodiment of the invention.

FIG. 13 illustrates three opening points 431, 432 and 433 and their corresponding opaque points 434, 435 and 436 respectively.

Points 431 and 434 are positioned on axis 428, points 432 and 435 are positioned on axis 427, and points 433 and 436 are positioned on axis 426. Axes 436, 437 and 438 are parallel to axis of symmetry 429.

It should be noted that the axis of asymmetry and axis of asymmetry can be oriented in other manners (for example—not oriented in 45 degrees and/or −45 degrees). The orientation may be set according to the expected or actual orientation of the detects of interest.

For example—aperture stop 410 was designed to inspect defects that are expected to be oriented along the X-axis and/or the Y-axis (corresponding to orientation of zero and ninety degrees).

The shape and orientation of the triangle shaped opening 424 and a trapezoid shaped opening 422 allow to receive non-specular reflections from defects that are horizontal or vertical.

Figure 14:
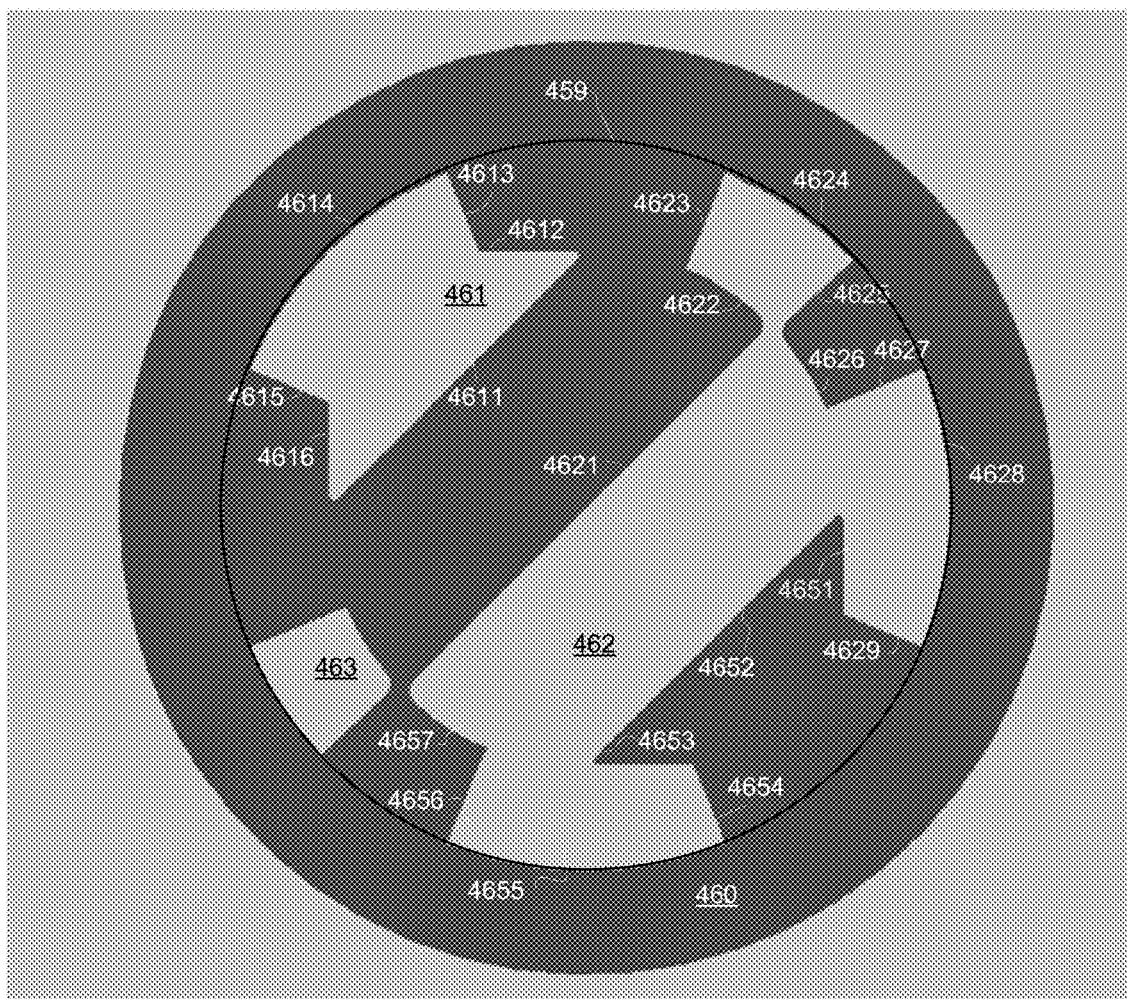
FIG. 14 illustrates an aperture stop according to an embodiment of the invention.
Figure 15:
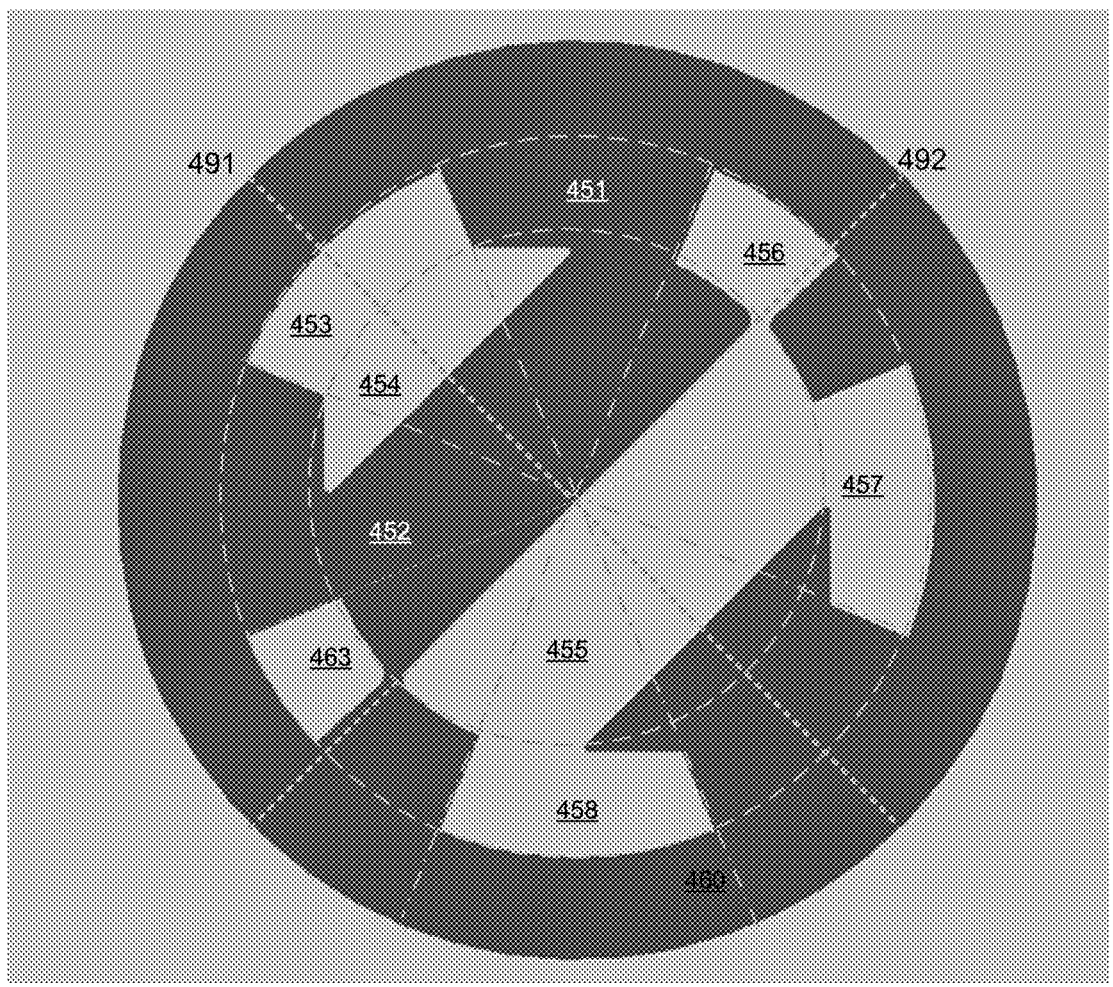
FIG. 15 illustrates an aperture stop according to an embodiment of the invention.
Figure 16:
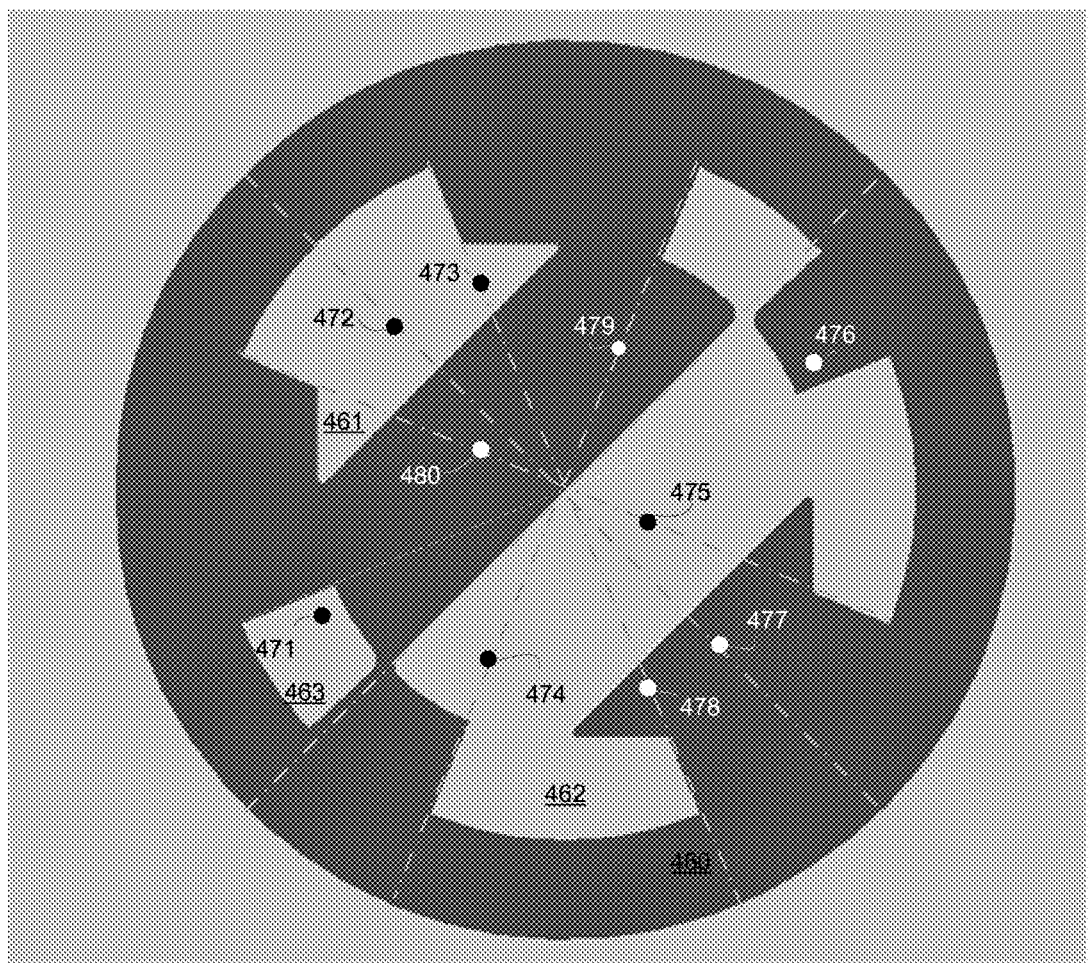
FIG. 16 illustrates an aperture stop according to an embodiment of the invention.

FIGS. 14-16 illustrate an aperture stop 450 according to an embodiment of the invention.

The aperture stop 450 is an example of an aperture stop that is not spiral and differs from an approximation of a spiral.

Aperture stop 450 includes three openings 461, 462 and 463. It is noted that opening 463 and 462 may be combined and that aperture portion 465 (see FIG. 15) can be separated from other portions of aperture 462.

Aperture stop 450 has an axis of symmetry 492 and an axis of asymmetry 491. The symmetry is an approximated symmetry—as aperture 463 and aperture portion 465 differ from each other by their relationship to aperture portion 455.

Aperture stop 450 was also designed to inspect defects that are expected to be oriented along the X-axis and/or the Y-axis (corresponding to orientation of zero and ninety degrees).

Figure 17:
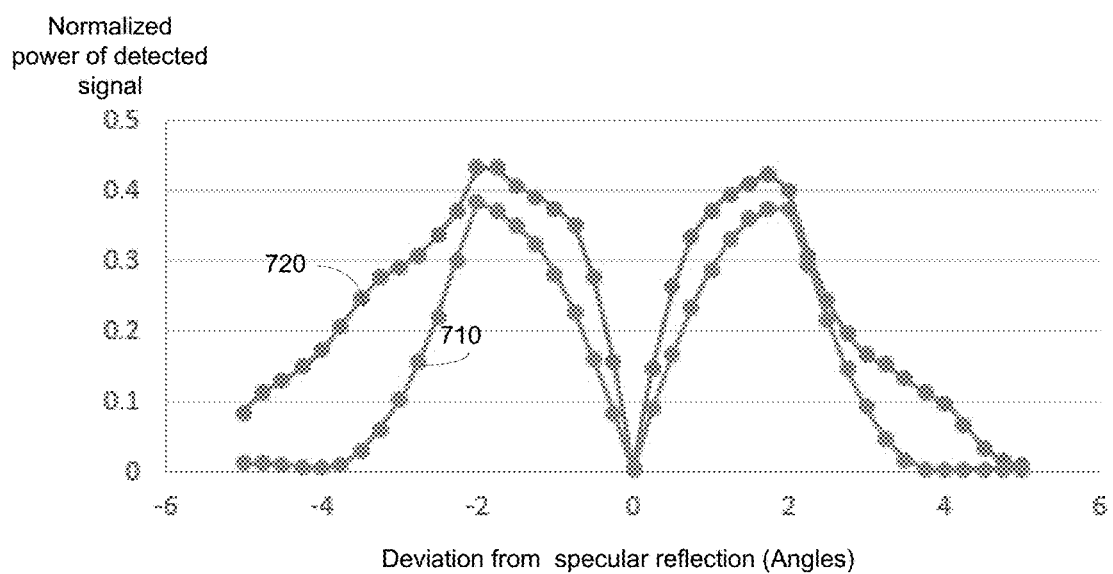
FIG. 17 illustrates a relationship between a normalized power of a detected signal and an angular deviation from specular reflection according to an embodiment of the invention.

Aperture stop 450 (see FIG. 17) passes more (attenuates less) reflected signals at angular deviation (in relation to specular reflection) of 1-5 degrees—in relation to aperture stop 410. See curve 720 (related to aperture stop 450) versus curve 710 (related to apertures top 410) of FIG. 17.

Circular region 459 of aperture stop may be formed of an interior circular portion 452 and an exterior ring 451 that surrounds the interior circular portion 452.

The various openings and/or opening portions that are located within interior circular portion 452 are referred to interior openings and/or interior opening portions respectively.

The various openings and/or opening portions that are located within exterior ring 451 are referred to exterior openings and/or exterior opening portions respectively.

Opening 462 has linear edge portions 4621, 4623, 4625, 4627, 4629, 4651, 4652, 4653, 4654, 4656 and non-linear edge portions 4622, 4624, 4626, 4628, 4655 and 4657.

Linear edge portions 4621, 4652 are parallel to the axis of asymmetry and are scant lines of interior circular region 452.

Linear edge portions 4623, 2625, 4627, 4629, 4654 and 4656 are parts of imaginary diameters of aperture stop 450.

Linear edge portions 4651 and 4653 are oriented (by less than ninety degrees) to the axis of asymmetry and are not a part of any diameter of aperture stop 450.

Opening 461 has linear edge portions 4611, 4613 and 4615 and non-linear edge portion 4614.

Linear edge portion 4611 is parallel to the axis of asymmetry and is a scant line of interior circular region 452.

Linear edge portions 4613 and 4613 are parts of imaginary diameters of aperture stop 450.

Linear edge portions 4612 and 4616 are oriented (by less than ninety degrees) to the axis of asymmetry and are not a part of any diameter of aperture stop 450.

Edge portions 4614, 4624, 4629 and 4655 may be a part of the exterior edge of exterior ring 451.

Edge portions 4622, 4651, 4653 and 4657 may be a part of the interior exterior edge of exterior ring 451 which is the exterior of the interior circular portion 452.

FIG. 16 illustrates five opening points 471, 472, 473, 474 and 475 and their corresponding opaque points 476, 477, 478, 478 and 480.

Each pair of opening point and corresponding opaque point are positioned on a diameter of aperture stop 450—at the same distance from the center of aperture stop 450—and at opposing sides.

It should be noted that the axis of asymmetry and axis of asymmetry can be oriented in other manners (for example—not oriented in 45 degrees and/or −45 degrees). The orientation may be set according to the expected or actual orientation of the detects of interest.

Those skilled in the art will recognize that boundaries between the functionality of the above described operations are merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Thus, it is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations, and alternatives are also possible. The specifications and drawings are, accordingly, to be regarded in an illustrative rather than in a restrictive sense.

The application is not limited to 2D and may expand to 3D inspection. The inspected substrate is not limited to a wafer and may include any type of substrate, especially flat substrates such as a printer circuit board, a solar panel, a MEMS device and the like.

The word "comprising" does not exclude the presence of other elements or steps then those listed in a claim. It is understood that the terms so used are interchangeable under appropriate circumstances such that the embodiments of the invention described herein are, for example, capable of operation in other orientations than those illustrated or otherwise described herein.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe.

Thus, these terms are not necessarily intended to indicate temporal or other prioritization of such elements. The mere fact that certain measures are recited in mutually different claims does not indicate that a combination of these measures cannot be used to advantage.

We claim:

1. An aperture stop comprising a circular region that comprises at least one opaque region and at least one opening region;

wherein each point in the at least one opening region is (a) mapped to an angle of illumination and (b) is associated with a corresponding point in the at least one opaque region that is mapped to an angle of specular reflectance from the angle of illumination mapped to the opening point;

wherein the at least one opening region comprises a first opening region that has a border that comprises at least one linear border portion and at least one non-linear border portion;

wherein the circular region comprises an interior circular portion that is surrounded by an exterior ring;

wherein a plurality of interior opening portions are positioned within the interior circular portion; and wherein a plurality of exterior opening portions are positioned within the exterior ring.

2. The aperture stop according to claim 1 wherein the first opening has a shape that differs from a combination of arcs.

3. The aperture stop according to claim 1 wherein the circular region has an axis of symmetry; wherein the multiple openings are symmetric in relation to the axis of symmetry.

4. The aperture stop according to claim 1 further comprising at least one opening within at least one of the interior circular portion and the exterior ring.

5. The aperture stop according to claim 1 wherein each one of the interior opening portions is delimited by at least one secant line and by an edge of the interior circular portion.

6. The aperture stop according to claim 1 wherein each one of the exterior opening portions is delimited by at least one radial line, by an interior edge and by an exterior edge of the exterior ring.

7. The aperture stop according to claim 1 wherein three exterior opening portions and two exterior openings are located within the exterior ring; and wherein two interior opening portions are located within the interior circular region.

8. The aperture stop according to claim 1 wherein the at least one linear border portion comprises a radial linear border portion and a linear border portion that is oriented to an axis of symmetry of the aperture stop and does not belong to any diameter of the aperture stop.

9. The aperture stop according to claim 8 wherein the aperture stop has a first axis of symmetry and a second axis of symmetry.

10. The aperture stop according to claim 1 wherein the first opening region comprises five linear border portions and a single non-linear border portion.

11. The aperture stop according to claim 1 wherein the first opening region comprises multiple linear border portions and multiple non-linear border portions.

12. The aperture stop according to claim 1 comprising a second opening region that has a border that comprises one or more linear border portions and one or more non-liner border portions.

13. The aperture stop according to claim 12 wherein the second opening region comprises three exterior opening portions and a single interior opening portion.

14. The aperture stop according to claim 13 wherein the single interior opening portion has an axis of symmetry and wherein two of the three exterior portions are positioned in a symmetrical manner in relation to the axis of symmetry.

15. The aperture stop according to claim 12 comprising a third second opening region that has a border that comprises one or more linear border portions and one or more non-liner border portions.

16. The aperture stop according to claim 15 wherein the third opening region has a single exterior opening portion.

17. An inspection system that comprises a light source, an objective lens and an aperture stop;

wherein the light source is configured to illuminate the aperture stop;

wherein the aperture stop is positioned at a stop of the objective lens;

wherein the aperture stop comprises a circular region that comprises at least one opaque region and at least one opening region;

wherein each point in the at least one opening region is (a) mapped to an angle of illumination and (b) is associated with a corresponding point in the at least one opaque region that is mapped to an angle of specular reflectance from the angle of illumination mapped to the opening point;

wherein the at least one opening region comprises a first opening region that has a border that comprises at least one linear border portion and at least one non-linear border portion;

wherein the circular region comprises an interior circular portion that is surrounded by an exterior ring;

wherein a plurality of interior opening portions are positioned within the interior circular portion; and wherein a plurality of exterior opening portions are positioned within the exterior ring.

18. The inspection system according to claim 17 wherein the first opening has a shape that differs from a combination of arcs.

19. The inspection system according to claim 17 wherein the circular region has an axis of symmetry; wherein the multiple openings are symmetric in relation to the axis of symmetry.

20. The inspection system according to claim 17 wherein the aperture stop further comprises at least one opening within at least one of the interior circular portion and the exterior ring.

21. The inspection system according to claim 17 wherein each one of the interior opening portions is delimited by at least one secant line and by an edge of the interior circular portion.

22. The inspection system according to claim 17 wherein each one of the exterior opening portions is delimited by at least one radial line, by an interior edge and by an exterior edge of the exterior ring.

23. The inspection system according to claim 17 wherein four exterior opening portions and an exterior opening are located within the exterior ring; and wherein two interior opening portions are located within the interior circular region.

24. A method, comprising:

illuminating an apertures stop that is located at a stop of an objective lens;

illuminating an object by light that passes through the aperture stop and an objective lens;

collecting, by the objective lens, reflected light that passes through the aperture stop, the reflected light differs from specular reflection light; and directing the reflected light that passes through the aperture stop towards a detector;

wherein the aperture stop comprises a circular region that comprises at least one opaque region and at least one opening region;

wherein each point in the at least one opening region is (a) mapped to an angle of illumination and (b) is associated with a corresponding point in the at least one opaque region that is mapped to an angle of specular reflectance from the angle of illumination mapped to the opening point;

wherein the at least one opening region comprises a first opening region that has a border that comprises at least one linear border portion and at least one non-linear border portion;

wherein the circular region comprises an interior circular portion that is surrounded by an exterior ring;

wherein a plurality of interior opening portions are positioned within the interior circular portion; and wherein a plurality of exterior opening portions are positioned within the exterior ring.

25. The method according to claim 24 wherein the first opening has a shape that differs from a combination of arcs.

26. The method according to claim 24 wherein the circular region has an axis of symmetry; wherein the multiple openings are symmetric in relation to the axis of symmetry.

27. The method according to claim 24 wherein the aperture stop further comprises at least one opening within at least one of the interior circular portion and the exterior ring.

28. The method according to claim 24 wherein each one of the interior opening portions is delimited by at least one secant line and by an edge of the interior circular portion.

29. The method according to claim 24 wherein each one of the exterior opening portions is delimited by at least one radial line, by an interior edge and by an exterior edge of the exterior ring.

30. The method according to claim 24 wherein four exterior opening portions and an exterior opening are located are located within the exterior ring; and wherein two interior opening portions are located within the interior circular region.

31. The method according to claim 24 wherein the at least one linear border portion comprises a radial linear border portion and a linear border portion that is oriented to an axis of symmetry of the aperture stop and does not belong to any diameter of the aperture stop.

32. The method according to claim 31 wherein the aperture stop has a first axis of symmetry and a second axis of symmetry.

33. The method according to claim 24 wherein the first opening region comprises five linear border portions and a single non-linear border portion.

34. The method according to claim 24 wherein the first opening region comprises multiple linear border portions and multiple non-linear border portions.

35. The method according to claim 24 comprising a second opening region that has a border that comprises one or more linear border portions and one or more non-liner border portions.

36. The method according to claim 35 wherein the second opening region comprises three exterior opening portions and a single interior opening portion.

37. The method according to claim 36 wherein the single interior opening portion has an axis of symmetry and wherein two of the three exterior portions are positioned in a symmetrical manner in relation to the axis of symmetry.

38. The method according to claim 35 comprising a third second opening region that has a border that comprises one or more linear border portions and one or more non-liner border portions.

39. The method according to claim 38 wherein the third opening region has a single exterior opening portion.

* * * * *